(12) United States Patent
Chen

(10) Patent No.: US 7,495,191 B2
(45) Date of Patent: Feb. 24, 2009

(54) LASER TREATMENT APPARATUS

(75) Inventor: Ga-Lane Chen, Santa Clara, CA (US)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 210 days.

(21) Appl. No.: 11/309,590

(22) Filed: Aug. 28, 2006

(65) Prior Publication Data

US 2007/0127029 A1  Jun. 7, 2007

(30) Foreign Application Priority Data

Dec. 2, 2005 (TW) .............................. 94142493 A

(51) Int. Cl.
*B23K 26/00* (2006.01)
*B23K 26/073* (2006.01)
*G01N 21/55* (2006.01)

(52) U.S. Cl. ..................... 219/121.73; 219/121.68; 250/459.1; 356/237.1

(58) Field of Classification Search ............. 356/237.1, 356/600–601; 250/458.1, 459.1; 219/121.73–121.77, 219/121.61–121.62, 121.68–121.69; 607/89, 607/90–92; 436/518
See application file for complete search history.

(56) References Cited

U.S. PATENT DOCUMENTS

| | | | | |
|---|---|---|---|---|
| 4,503,854 A | * | 3/1985 | Jako | 606/11 |
| 5,103,073 A | * | 4/1992 | Danilov et al. | 219/121.68 |
| 5,164,565 A | * | 11/1992 | Addiego et al. | 219/121.68 |
| 6,049,057 A | * | 4/2000 | Imai et al. | 219/121.7 |
| 6,541,731 B2 | * | 4/2003 | Mead et al. | 219/121.7 |
| 6,582,454 B2 | * | 6/2003 | Yayama | 607/89 |
| 6,750,423 B2 | * | 6/2004 | Tanaka et al. | 219/121.73 |
| 6,911,623 B2 | | 6/2005 | Ito | |
| 6,936,829 B2 | * | 8/2005 | Nishioka | 250/459.1 |
| 7,326,630 B2 | * | 2/2008 | Tanaka et al. | 438/487 |
| 2002/0028521 A1 | * | 3/2002 | Ogura | 436/518 |

* cited by examiner

Primary Examiner—Sang Nguyen
(74) Attorney, Agent, or Firm—Frank R. Niranjan

(57) ABSTRACT

A laser treatment apparatus, configured for treating a workpiece, includes: a first laser generation device, a first optical assembly, a second laser generation device, a second optical assembly, a third laser generation device, and an optical detection device. The first optical assembly is configured for directing a first laser beam generated by the first laser generation device onto a first target of the workpiece. The second optical assembly is configured for directing a second laser beam generated by the second laser generation onto a second target of the workpiece. The first laser beam has a wavelength different from that of the second laser beam. The third laser generation device is configured for generating a third laser beam to strike on the first target and/or the second target. The optical detection device is configured for detecting a reflection part of the third laser beam reflected from the workpiece.

20 Claims, 1 Drawing Sheet

LASER TREATMENT APPARATUS

FIELD OF THE INVENTION

This invention relates generally to laser treatment apparatuses and, more particularly, to high precision laser treatment apparatuses for mass application.

DESCRIPTION OF RELATED ART

Nowadays, laser radiation has been widely used in a large variety of applications, such as welding, slicing, cutting and drilling, due to its faster speed and higher precision. Laser treatment techniques using laser radiation can be used to process various types of materials, such as metal, plastic, glass and ceramic. Due to different absorption wavelengths for different kinds of materials, different laser treatment apparatuses with suitable laser wavelengths are required. For instance, for treatment of metal or plastic materials, solid-state lasers are generally employed; for processing glass or ceramic materials, carbon dioxide lasers are usually used.

However, a workpiece made of a composite material, having multiple compositions and, thus, multiple absorption wavelengths, generally requires multiple laser treatment apparatuses, each with a characteristic wavelength associated therewith, working together cooperatively to finish the work. The workpiece needs to be repeatedly moved from one such laser treatment apparatus to another one by, e.g., an operator or a programmable controller and must, accordingly, be realigned in each laser treatment apparatus, which is a time consuming process and may result in a loss of treatment accuracy.

What is needed is to provide a laser treatment apparatus with a relatively higher efficiency that can still accommodate materials/composites having different absorption wavelengths.

SUMMARY OF THE INVENTION

A preferred embodiment provides a laser treatment apparatus configured for treatment of a workpiece. The laser treatment apparatus includes: a first laser generation device, a first optical assembly, a second laser generation device, a second optical assembly, a third laser generation device, and an optical detection device. The first laser generation device is configured (i.e., structured and arranged) for generating a first laser beam having a first wavelength. The first optical assembly is configured for directing the first laser beam onto a first target of the workpiece, the first target having an absorption wavelength matching with the first wavelength. The second laser generation device is configured for generating a second laser beam, the second laser beam having a second wavelength different from the first wavelength. The second optical assembly is configured for directing the second laser beam onto a second target of the workpiece, the second target having an absorption wavelength matching with the second wavelength. The third laser generation device is configured for generating a third laser beam to strike on the first target and/or the second target of the workpiece. The optical detection device is configured for detecting a reflection part of the third laser beam reflected from the workpiece to output a monitoring signal.

The laser treatment apparatus in accordance with the preferred embodiment incorporates multiple laser generation devices working together therein, which facilitates simultaneous processing and monitoring of a workpiece. Such simultaneous processing and monitoring allows the workpiece to be completely treated by such an integrated laser treatment apparatus and to thus achieve a relatively higher level of production efficiency.

Other advantages and novel features will become more apparent from the following detailed description of embodiments when taken in conjunction with the accompanying drawings.

BRIEF DESCRIPTION OF THE DRAWINGS

Many aspects of the present laser treatment apparatus can be better understood with reference to the following drawings. The components in the drawings are not necessarily drawn to scale, the emphasis instead being placed upon clearly illustrating the principles of the present apparatus. Moreover, in the drawings, like reference numerals designate corresponding parts throughout the several views.

Figure 1:
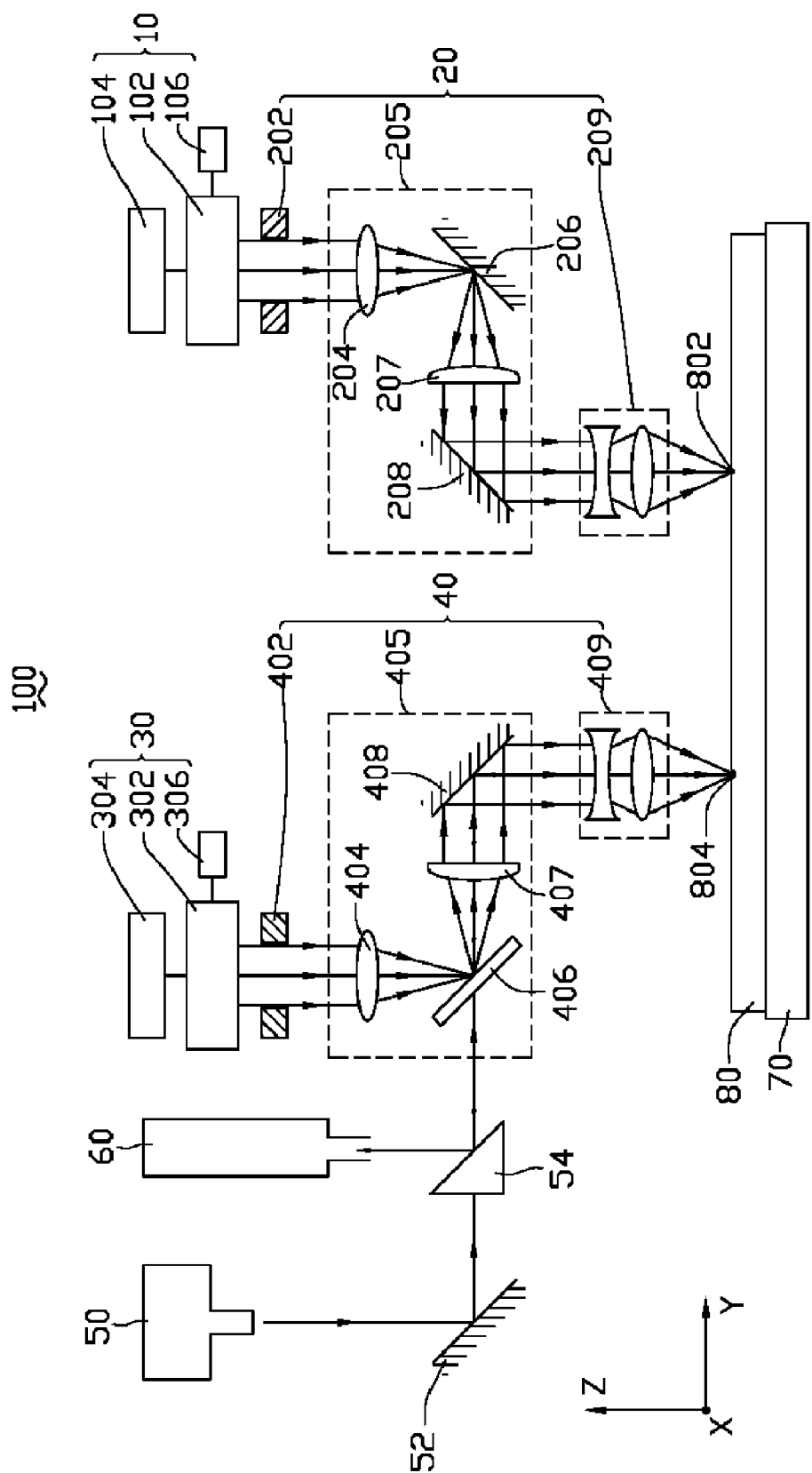
FIG. 1 is a schematic view of a laser treatment apparatus in accordance with a preferred embodiment.

The exemplifications set out herein illustrate at least one preferred embodiment, in one form, and such exemplifications are not to be construed as limiting the scope of the present laser treatment apparatus in any manner.

DETAILED DESCRIPTION OF THE INVENTION

Referring to FIG. 1, a laser treatment apparatus 100, in accordance with a preferred embodiment, is provided. The laser treatment apparatus 100 includes: a first laser generation device 10, a first optical assembly 20, a second laser generation device 30, a second optical assembly 40, a third laser generation device 50, an optical detection device 60, and a movable workstation 70.

The first laser generation device 10 is configured for generating a first laser beam. The first laser beam can be employed to process a material having a relatively long absorption wavelength, such as glasses and ceramics. The first laser beam, as per this embodiment, has a wavelength $\lambda 1$ in the approximate range from 2.4 to 15 micrometers.

The first laser generation device 10 includes a laser oscillator 102, a controller 104, and a cooler 106. The laser oscillator 102 is configured for emitting the first laser beam. The laser oscillator 102 advantageously is a molecular laser oscillator, such as a carbon dioxide laser oscillator. Typically, a carbon dioxide laser oscillator can emit a laser beam at a wavelength of 10.6 micrometers and has an output power about in the range from 5 watts to 25 kilowatts. The carbon dioxide laser oscillator can be carried out in a continuous wave mode. The controller 104 is configured (i.e., structured and arranged) for setting operational parameters for the laser oscillator 102. The cooler 106 is configured for dissipating heat generated by the laser oscillator 102 during operation thereof.

The first optical assembly 20 is configured for directing/focusing the first laser beam to a first target 802 of a workpiece 80, the first target 802 having an absorption wavelength matching with the wavelength $\lambda 1$. The first optical assembly 20, along a propagation path of the first laser beam, includes a blocking shutter 202, a converging lens 204, a first deflecting member 206 (e.g., a total reflection mirror), a focusing lens 207, a second deflecting member 208 (e.g., a total reflection mirror), and a zoom lens 209, in sequence. The blocking shutter 202 is configured for adjusting a spot size of the first laser beam emitted from the first laser generation device 10. The converging lens 204, the first deflecting member 206, the focusing lens 207, and the second deflecting member 208 constitute a first deflection assembly 205 for guiding the first laser beam to strike on the zoom lens 209. It should be understood that the first deflection assembly 205 could have other suitable configurations that will suitably facilitate the guidance of the first laser beam to strike on the zoom lens 209. The zoom lens 209 is configured for receiving the first laser beam delivered by the first deflection assembly 205 and focusing the first laser beam on the first target 802 of the workpiece 80. Alternatively, the first laser beam generated by the first laser generation device 10 can be directly incident on the zoom lens 209, thus precluding the blocking shutter 202 and/or the first deflection assembly 205 (i.e., one or both such elements 202, 205 can be optional).

The second laser generation device 30 is configured for generating a second laser beam. The second laser beam can be employed to process a material having a relatively short absorption wavelength, such as metal and plastic. The second laser beam of this embodiment has a wavelength $\lambda 2$ in the range from about 200 to about 1200 nanometers. It is to be understood that the positions of the first and second laser generation devices 10 and 30 could be switched and still be within the scope of the present laser system. The key is having at least one of each of the first and second laser generation devices 10 and 30 available in the system, so that the system can accommodate materials with short absorption wavelengths and materials with long absorption wavelengths.

The second laser generation device 30 includes a laser oscillator 302, a controller 304, and a cooler 306. The laser oscillator 302 is configured for emitting the second laser beam. The laser oscillator 302 is, beneficially, a solid-state laser oscillator, and preferably is a diode-pumped solid-state laser oscillator, e.g., a diode-pumped neodymium-doped yttrium-aluminum garnet (Nd:YAG) laser oscillator or a diode-pumped neodymium-doped yttrium orthovanadate (Nd:YVO4) laser oscillator, equipped with a frequency-doubler. The frequency-doubler can, e.g., be a potassium dihydrogen phosphate (KDP) Pockels cell. Typically, the diode-pumped solid-state oscillator equipped with the frequency-doubler can emit a laser beam at a wavelength of 532 nanometers and has an output power in the approximate range from 1 milliwatt to 5 kilowatts. The diode-pumped solid-state laser oscillator can be carried out in a pulse wave mode. The controller 304 is configured for setting operational parameters of the laser oscillator 302, such as pulse energy, pulse duration, and pulse repetition rate. The cooler 306 is configured for dissipating heat generated, in operation, by the laser oscillator 302.

The second optical assembly 40 is configured for directing the second laser beam to a second target 804 of the workpiece 80, the second target 804 having an absorption wavelength matching with the wavelength $\lambda 2$. The second optical assembly 40, along a propagation path of the second laser beam, includes a blocking shutter 402, a focusing lens 404, a dichroic lens 406, a converging lens 407, a deflecting member 408 (e.g., a total reflection mirror), and a zoom lens 409, in sequence. The blocking shutter 402 is configured for selectably adjusting a spot size of the second laser beam emitted from the second laser generation device 30. The focusing lens 404, the dichroic lens 406, the converging lens 407, and the deflecting member 408 constitute a second deflection assembly 405 for guiding the second laser beam to strike on the zoom lens 409. It should be understood that the second deflection assembly 405 could have other suitable configurations that will suitably facilitate the guidance of the second laser beam to strike on the zoom lens 409. The zoom lens 409 is configured for receiving the second laser beam delivered by the second deflection assembly 405 and thereby focusing the second laser beam on the second target 804. Alternatively, the second laser beam generated by the second laser generation device 30 can be directly incident on the zoom lens 409, without the blocking shutter 402 and the second deflection assembly 405 present.

The third laser generation device 50 is configured for generating a third laser beam. The third laser beam can be used as a detection light to measure a treated state of the first target 802 and/or the second target 804 of the workpiece 80. The third laser beam, beneficially, has a wavelength about in the visible light range, i.e., 380 to 780 nanometers, for cost saving. The third laser generation device 50 usually includes an atomic gas laser oscillator or an ion gas laser oscillator. Typically, a helium-neon (He—Ne) laser oscillator (i.e., one kind of atomic gas laser oscillator) can emit a laser beam at a wavelength of 632.5 nanometers and has an output power about in the range from 0.5 to 100 milliwatts.

The optical detection device 60 is configured for detecting a reflection part of the third laser beam, as reflected from the workpiece 80, for the purpose of outputting a monitoring signal representing a treated state (e.g., surface completion) of the first target 802 and/or second target 804 of the workpiece 80. The monitoring signal can be used as a reference for optimizing operational parameters of the first laser generation device 10 and/or the second laser generation device 30. The optical detection device 60 can include a camera and/or a monitor device.

In the illustrated embodiment, the first target 802 and the second target 804 of the workpiece 80 are supported by the workstation 70 and are treated, respectively, by the first laser beam and the second laser beam. The third laser beam generated from the third laser generation device 50 is used as a detection light to measure a treated state of the first target 802 and/or the second target 804 of the workpiece 80. The third laser beam is delivered by a deflecting member 52 (e.g., a total reflection mirror), a prism 54, the second deflection assembly 405 except for the focusing lens 404 thereof (i.e., the dichroic lens 406, the converging lens 407, and the deflecting member 408), and the zoom lens 409, in that order. Upon traversing such elements in the order described, the third laser beam, as particularly illustrated, is then incident on the second target 804 of the workpiece 80 to measure a treated state (e.g., surface completion) of the second target 804. Subsequently, at least a part (hereinafter also referred to as the reflection part) of the third laser beam is reflected by the second target 804 and is delivered back by the zoom lens 409, the second deflection assembly 405 except for the focusing lens 404 thereof, and the prism 54, in that order. The reflection part of the third laser beam, as reflected by the prism 54, would be detected by means of the optical detection device 60. As an illustration, the dichroic lens 406 can selectively reflect the third laser beam and transmit the second laser beam. It should be understood that the position of the deflecting member 408 can be exchanged with that of the dichroic lens 406, and, correspondingly, the deflecting member 52 and the prism can be kept adjacent to the dichroic lens.

It should be understood that the third laser beam could, as mentioned above, also be used to measure a treated state of the first target 802. Correspondingly, the deflecting member 52 and the prism 54 would be disposed adjacent to the first deflecting member 206 of the first optical assembly 20 to achieve that goal. Additionally, the first deflecting member 206 could be a dichroic lens, which could selectively reflect the third laser beam and transmit the first laser beam. Alternatively, the deflecting member 52 and the prism 54 could be disposed adjacent to the second deflecting member 208 of the first optical assembly 20, and the second deflecting member 206 could be a dichroic lens.

The workstation 70 is movable and is configured for supporting the workpiece 80 and moving the first target 802 and/or the second target 804 of the workpiece 80 to be treated by a corresponding laser generation device (i.e., the first laser generation device 10 and/or the second laser generation device 30). The workstation 70 can move along the X, Y, and Z directions in a Cartesian coordinate system; and/or rotate around and/or tilt along an axis (not labeled) parallel/coextensive with the X or Y direction (i.e., linearly, rotationally, and/or angularly).

It is believed that the present embodiments and their advantages will be understood from the foregoing description, and it will be apparent that various changes may be made thereto without departing from the spirit and scope of the invention or sacrificing all of its material advantages, the examples hereinbefore described merely being preferred or exemplary embodiments of the present invention.

What is claimed is:

1. A laser treatment apparatus configured for treating a workpiece, comprising:
   a first laser generation device configured for generating a first laser beam having a first wavelength;
   a first optical assembly configured for directing the first laser beam onto a first target of the workpiece, the first target having an absorption wavelength matching with the first wavelength;
   a second laser generation device configured for generating a second laser beam, the second laser beam having has a second wavelength different from the first wavelength;
   a second optical assembly configured for directing the second laser beam onto a second target of the workpiece, the second target having an absorption wavelength matching with the second wavelength;
   a third laser generation device configured for generating a third laser beam to selectably strike onto one of the first target and the second target of the workpiece; and
   an optical detection device configured for detecting a reflection part of the third laser beam reflected from the workpiece and for outputting a monitoring signal based upon the detected reflection part of the third laser beam;
   wherein the at least one of the first optical assembly and the second optical assembly comprises
   a focusing lens,
   a blocking shutter configured for adjusting a spot size of a corresponding laser beam before being incident onto the corresponding one of the focusing lens of the first optical assembly and the focusing lens of the second optical assembly, and
   a deflection assembly interposed between the blocking shutter and the focusing lens, the deflection assembly, along a direction oriented from the blocking shutter to the focusing lens, comprising another focusing lens, a first deflecting member, a converging lens, and a second deflecting member, the deflection assembly being configured for deflecting a propagation direction of the corresponding laser beam and guiding the corresponding laser beam to strike on the corresponding one of the focusing lens of the first optical assembly and the focusing lens of the second optical assembly.

2. The laser treatment apparatus of claim 1, wherein the first wavelength of the first laser beam generated by the first laser generation device is in the approximate range from 2.4 to 15 micrometers.

3. The laser treatment apparatus of claim 2, wherein the first laser generation device comprises a molecular gas laser oscillator configured for emitting the first laser beam.

4. The laser treatment apparatus of claim 1, wherein the second wavelength of the second laser beam generated by the second laser generation device is about in the range from 200 to 1200 nanometers.

5. The laser treatment apparatus of claim 4, wherein the second laser generation device comprises a solid-state laser oscillator configured for emitting the second laser beam.

6. The laser treatment apparatus of claim 5, wherein the solid-state laser oscillator is a diode-pumped solid-state laser oscillator equipped with a frequency doubler.

7. The laser treatment apparatus of claim 1, wherein a wavelength of the third laser beam generated by the third laser generation device is in the visible range.

8. The laser treatment apparatus of claim 7, wherein the third laser generation device comprises one of an atomic gas laser oscillator and an ion gas laser oscillator.

9. The laser treatment apparatus of claim 1, further comprising a workstation configured for supporting the workpiece and moving the workpiece, the workstation being configured for selectably moving at least one of linearly, rotationally, and angularly.

10. The laser treatment apparatus of claim 1, wherein the focusing lens is a zoom lens.

11. The laser treatment apparatus of claim 1, wherein the first deflecting member is a dichroic lens.

12. The laser treatment apparatus of claim 11, further comprising a third deflecting member and a prism, the prism being configured for transmitting the third laser beam reflected by the third deflecting member to strike on the dichroic lens and reflecting the reflection part of the third laser beam into the optical detection device.

13. A laser treatment apparatus configured for treating a workpiece, comprising:
   a first laser generation device configured for generating a first laser beam having a first wavelength;
   a first optical assembly configured for directing the first laser beam onto a first target of the workpiece, the first target having an absorption wavelength matching with the first wavelength;
   a second laser generation device configured for generating a second laser beam, the second laser beam having a second wavelength different from the first wavelength;
   a second optical assembly configured for directing the second laser beam onto a second target of the workpiece, the second target having an absorption wavelength matching with the second wavelength, the second optical assembly comprising a dichroic lens;
   a third laser generation device configured for generating a third laser beam;
   a prism configured for transmitting the third laser beam to strike on the dichroic lens and then be selectably incident onto one of the first target and the second target of the workpiece, a reflection part of the third laser beam being first reflected from the workpiece and delivered back to the prism by the dichroic lens, the prism also being configured for further reflecting the reflection part of the third laser beam; and
   an optical detection device configured for detecting the reflection part reflected by the prism and for outputting a monitoring signal based upon the detected reflection part.

14. The laser treatment apparatus of claim 13, wherein the first wavelength of the first laser beam generated by the first laser generation device is in the approximate range from 2.4 to 15 micrometers.

15. The laser treatment apparatus of claim 14, wherein the first laser generation device comprises a molecular gas laser oscillator configured for emitting the first laser beam.

16. The laser treatment apparatus of claim 13, wherein the second wavelength of the second laser beam generated by the second laser generation device is about in the range from 200 to 1200 nanometers.

17. The laser treatment apparatus of claim 16, wherein the second laser generation device comprises a solid-state laser oscillator configured for emitting the second laser beam.

18. The laser treatment apparatus of claim 17, wherein the solid-state laser oscillator is a diode-pumped solid-state laser oscillator equipped with a frequency doubler.

19. The laser treatment apparatus of claim 13, wherein a wavelength of the third laser beam generated by the third laser generation device is in the visible range.

20. The laser treatment apparatus of claim 19, wherein the third laser generation device comprises one of an atomic gas laser oscillator and an ion gas laser oscillator.

* * * * *